(12) United States Patent
Bizup et al.

(10) Patent No.: US 11,878,137 B2
(45) Date of Patent: *Jan. 23, 2024

(54) VENOUS ACCESS PORT ASSEMBLY WITH X-RAY DISCERNABLE INDICIA

(71) Applicant: Medical Components, Inc., Harleysville, PA (US)

(72) Inventors: Raymond Bizup, Feasterville, PA (US); Kevin Sanford, Chalfont, PA (US); Christopher Linden, Vista, CA (US); Kenneth M. Zinn, Westport, CT (US); Timothy M. Schweikert, West Chester, PA (US)

(73) Assignee: Medical Components, Inc., Harleysville, PA (US)

( * ) Notice: Subject to any disclaimer, the term of this patent is extended or adjusted under 35 U.S.C. 154(b) by 370 days.

This patent is subject to a terminal disclaimer.

(21) Appl. No.: 17/122,251

(22) Filed: Dec. 15, 2020

(65) Prior Publication Data

US 2021/0093847 A1 Apr. 1, 2021

Related U.S. Application Data

(63) Continuation of application No. 15/251,122, filed on Aug. 30, 2016, now Pat. No. 10,874,842, which is a
(Continued)

(51) Int. Cl.
*A61M 39/02* (2006.01)
*A61M 39/04* (2006.01)
*A61M 39/00* (2006.01)

(52) U.S. Cl.
CPC ........ *A61M 39/0208* (2013.01); *A61M 39/04* (2013.01); *A61M 2039/0009* (2013.01);
(Continued)

(58) Field of Classification Search
CPC .............. A61M 39/0208; A61M 39/04; A61M 2205/04; A61M 2039/0009;
(Continued)

(56) References Cited

U.S. PATENT DOCUMENTS 574,387 A 12/1899 Buckler
611,357 A 12/1899 Dembinski
(Continued)

FOREIGN PATENT DOCUMENTS

CA 2663853 A1 4/2008
CA 2663853 C 11/2014
(Continued)

OTHER PUBLICATIONS 9.75/1 0.0 em Lap-Band System vs. 11 em Lap-Band System: For Product Manufactured Prior to Jul. 2001, Lap-Band System Access Port Fill Guide I BioEnterics Corporation, Jul. 1, 2001, 1 page.
(Continued)

*Primary Examiner* — Bradley J Osinski

(57) ABSTRACT

A venous access port assembly having a housing base with a discharge port, a septum, and a cap, with an interior reservoir. The housing base is provided with X-ray discernable indicia to identify an attribute of the assembly after its implantation and clearly appear on an X-ray of the patient in a manner informing the radiologist or technologist and the medical practitioner of that particular attribute. Such indicia can be depicted as cutouts through a disc of radiopaque material where the cutouts are in the form of alphabetical letters such as "CT", or can be a set of discrete elements of radiopaque material, that are affixed along the bottom surface of the housing base or embedded within the thickness of the bottom housing wall.

30 Claims, 4 Drawing Sheets

Related U.S. Application Data continuation of application No. 13/088,762, filed on Apr. 18, 2011, now Pat. No. 9,517,329, which is a continuation of application No. 12/175,182, filed on Jul. 17, 2008, now Pat. No. 8,021,324, which is a continuation-in-part of application No. 11/725,287, filed on Mar. 19, 2007, now abandoned.

(60) Provisional application No. 60/961,133, filed on Jul. 19, 2007, provisional application No. 60/852,591, filed on Oct. 18, 2006.

(52) U.S. Cl.
CPC .............. *A61M 2039/0045* (2013.01); *A61M 2039/0205* (2013.01); *A61M 2039/0238* (2013.01); *A61M 2205/04* (2013.01); *A61M 2205/32* (2013.01)

(58) Field of Classification Search
CPC .. A61M 2039/0045; A61M 2039/0238; A61M 2205/32
See application file for complete search history.

(56) References Cited

U.S. PATENT DOCUMENTS

| | | |
|---|---|---|
| 966,696 A | 8/1910 | Merrill |
| 1,713,267 A | 5/1929 | Crowley |
| 2,029,553 A | 2/1936 | Bartschi et al. |
| 2,433,480 A | 12/1947 | Rendich |
| 2,891,689 A | 6/1959 | Gould |
| D198,453 S | 6/1964 | Weichselbaum |
| 3,293,663 A | 12/1966 | Cronin |
| 3,341,417 A | 9/1967 | Sinaiko |
| 3,518,428 A | 6/1970 | Ring |
| 3,529,633 A | 9/1970 | Vaillancourt |
| 3,631,563 A | 1/1972 | Snowden |
| 3,643,358 A | 2/1972 | Morderosian |
| 3,829,904 A | 8/1974 | Ling et al. |
| 3,831,583 A | 8/1974 | Edmunds et al. |
| 3,840,009 A | 10/1974 | Michaels et al. |
| 3,891,997 A | 7/1975 | Herbert |
| 3,915,162 A | 10/1975 | Miller |
| 3,919,724 A | 11/1975 | Sanders et al. |
| 3,922,726 A | 12/1975 | Trentani et al. |
| 3,951,147 A | 4/1976 | Tucker et al. |
| 4,027,391 A | 6/1977 | Samis |
| 4,035,653 A | 7/1977 | Karasko |
| 4,121,108 A | 10/1978 | Manor |
| 4,123,806 A | 11/1978 | Amstutz et al. |
| 4,168,586 A | 9/1979 | Samis |
| 4,181,132 A | 1/1980 | Parks |
| 4,190,040 A | 2/1980 | Schulte |
| 4,190,057 A | 2/1980 | Downie et al. |
| 4,194,122 A | 3/1980 | Mitchell et al. |
| 4,202,349 A | 5/1980 | Jones |
| 4,222,374 A | 9/1980 | Sampson et al. |
| 4,233,964 A | 11/1980 | Jefferts et al. |
| 4,274,006 A | 6/1981 | Caine |
| 4,349,498 A | 9/1982 | Ellis et al. |
| 4,361,153 A | 11/1982 | Slocum et al. |
| 4,405,305 A | 9/1983 | Stephen et al. |
| 4,406,567 A | 9/1983 | Samis |
| 4,425,119 A | 1/1984 | Berglund |
| 4,445,896 A | 5/1984 | Gianturco |
| 4,450,592 A | 5/1984 | Niederer et al. |
| 4,450,985 A | 5/1984 | Beard |
| 4,456,011 A | 6/1984 | Warnecke |
| 4,469,483 A | 9/1984 | Becker et al. |
| 4,494,545 A | 1/1985 | Slocum et al. |
| 4,506,676 A | 3/1985 | Duska |
| 4,529,635 A | 7/1985 | Sheldon |
| 4,543,088 A | 9/1985 | Bootman et al. |
| 4,549,879 A | 10/1985 | Groshong et al. |
| 4,559,043 A | 12/1985 | Whitehouse et al. |
| 4,559,046 A | 12/1985 | Groshong et al. |
| 4,560,375 A | 12/1985 | Schulte et al. |
| 4,571,749 A | 2/1986 | Fischell |
| 4,576,595 A | 3/1986 | Aas et al. |
| 4,587,954 A | 5/1986 | Haber |
| 4,612,877 A | 9/1986 | Hayes et al. |
| 4,627,844 A | 12/1986 | Schmitt |
| 4,634,427 A | 1/1987 | Hannula et al. |
| 4,636,194 A | 1/1987 | Schulte et al. |
| 4,636,213 A | 1/1987 | Pakiam |
| 4,645,495 A | 2/1987 | Vaillancourt |
| 4,653,508 A | 3/1987 | Cosman |
| 4,655,765 A | 4/1987 | Swift |
| 4,657,024 A | 4/1987 | Coneys |
| 4,662,652 A | 5/1987 | Hargis |
| 4,668,221 A | 5/1987 | Luther |
| 4,671,796 A | 6/1987 | Groshong et al. |
| 4,673,394 A | 6/1987 | Fenton et al. |
| 4,684,365 A | 8/1987 | Reinicke |
| 4,685,447 A | 8/1987 | Iversen et al. |
| 4,685,905 A | 8/1987 | Jeanneret |
| 4,692,146 A | 9/1987 | Hilger |
| 4,695,273 A | 9/1987 | Brown |
| 4,697,595 A | 10/1987 | Breyer et al. |
| 4,701,166 A | 10/1987 | Groshong et al. |
| 4,704,103 A | 11/1987 | Stoeber et al. |
| 4,710,174 A | 12/1987 | Moden et al. |
| 4,718,894 A | 1/1988 | Lazorthes |
| 4,728,894 A | 3/1988 | Yoda et al. |
| 4,743,231 A | 5/1988 | Kay et al. |
| 4,753,640 A | 6/1988 | Nichols et al. |
| 4,755,173 A | 7/1988 | Konopka et al. |
| 4,760,837 A | 8/1988 | Petit |
| 4,762,517 A | 8/1988 | Mcintyre et al. |
| 4,767,410 A | 8/1988 | Moden et al. |
| 4,772,270 A | 9/1988 | Wiita et al. |
| 4,772,276 A | 9/1988 | Wiita et al. |
| 4,773,552 A | 9/1988 | Boege et al. |
| 4,778,452 A | 10/1988 | Moden et al. |
| 4,781,680 A | 11/1988 | Redmond et al. |
| 4,781,685 A | 11/1988 | Lehmann et al. |
| 4,781,695 A | 11/1988 | Dalton |
| 4,802,885 A | 2/1989 | Weeks et al. |
| 4,804,054 A | 2/1989 | Howson et al. |
| 4,820,273 A | 4/1989 | Reinicke |
| 4,822,341 A | 4/1989 | Colone |
| 4,840,615 A | 6/1989 | Hancock et al. |
| 4,848,346 A | 7/1989 | Crawford |
| 4,857,053 A | 8/1989 | Dalton |
| 4,861,341 A | 8/1989 | Woodburn |
| 4,863,470 A | 9/1989 | Carter |
| 4,886,501 A | 12/1989 | Johnston et al. |
| 4,892,518 A | 1/1990 | Cupp et al. |
| 4,904,241 A | 2/1990 | Bark |
| 4,905,709 A | 3/1990 | Bieganski et al. |
| 4,909,250 A | 3/1990 | Smith |
| 4,915,690 A | 4/1990 | Cone et al. |
| 4,928,298 A | 5/1990 | Tanaka |
| 4,929,236 A | 5/1990 | Sampson |
| 4,955,861 A | 9/1990 | Enegren et al. |
| 4,963,133 A | 10/1990 | Whipple |
| 4,966,583 A | 10/1990 | Debbas |
| 4,973,319 A | 11/1990 | Melsky |
| 4,983,162 A | 1/1991 | Metais et al. |
| 5,002,735 A | 3/1991 | Alberhasky et al. |
| 5,009,644 A | 4/1991 | Mcdonald |
| 5,013,298 A | 5/1991 | Moden et al. |
| 5,041,098 A | 8/1991 | Loiterman et al. |
| 5,044,955 A | 9/1991 | Jagmin |
| 5,045,060 A | 9/1991 | Melsky et al. |
| 5,045,064 A | 9/1991 | Idriss |
| 5,084,015 A | 1/1992 | Moriuchi |
| 5,085,216 A | 2/1992 | Henley et al. |
| 5,090,066 A | 2/1992 | Schoepe et al. |
| 5,092,849 A | 3/1992 | Sampson |
| 5,108,317 A | 4/1992 | Beinhaur et al. |
| 5,108,377 A | 4/1992 | Cone et al. |
| 5,112,301 A | 5/1992 | Fenton et al. |

(56) References Cited

U.S. PATENT DOCUMENTS

| | | |
|---|---|---|
| 5,112,303 A | 5/1992 | Pudenz et al. |
| 5,129,891 A | 7/1992 | Young |
| 5,137,529 A | 8/1992 | Watson et al. |
| 5,147,483 A | 9/1992 | Melsky et al. |
| 5,152,753 A | 10/1992 | Laguette et al. |
| 5,156,600 A | 10/1992 | Young |
| 5,158,547 A | 10/1992 | Doan et al. |
| 5,167,629 A | 12/1992 | Vertenstein et al. |
| 5,167,633 A | 12/1992 | Mann et al. |
| 5,167,638 A | 12/1992 | Felix et al. |
| 5,171,228 A | 12/1992 | Mcdonald |
| 5,176,653 A | 1/1993 | Metals |
| 5,176,662 A | 1/1993 | Bartholomew et al. |
| 5,178,612 A | 1/1993 | Fenton, Jr. |
| 5,185,003 A | 2/1993 | Brethauer |
| 5,189,690 A | 2/1993 | Samuel |
| 5,193,106 A | 3/1993 | Desena |
| 5,195,122 A | 3/1993 | Fabian |
| 5,195,123 A | 3/1993 | Clement |
| 5,201,715 A | 4/1993 | Masters |
| 5,203,771 A | 4/1993 | Melker et al. |
| 5,203,777 A | 4/1993 | Lee |
| 5,213,574 A | 5/1993 | Tucker |
| 5,215,537 A | 6/1993 | Lynn et al. |
| 5,222,499 A | 6/1993 | Allen et al. |
| D337,637 S | 7/1993 | Tucker |
| 5,224,938 A | 7/1993 | Fenton, Jr. |
| 5,263,930 A | 11/1993 | Ensminger |
| 5,281,205 A | 1/1994 | Mcpherson |
| 5,290,263 A | 3/1994 | Wigness et al. |
| 5,295,658 A | 3/1994 | Atkinson et al. |
| 5,299,253 A | 3/1994 | Wessels |
| 5,309,863 A | 5/1994 | Leeb, Jr. |
| 5,312,337 A | 5/1994 | Flaherty et al. |
| 5,316,545 A | 5/1994 | Cherubini |
| 5,318,545 A | 6/1994 | Tucker |
| 5,320,100 A | 6/1994 | Herweck et al. |
| 5,322,511 A | 6/1994 | Armbruster et al. |
| 5,326,460 A | 7/1994 | Cheesman et al. |
| 5,328,480 A | 7/1994 | Melker et al. |
| 5,332,398 A | 7/1994 | Miller et al. |
| 5,334,153 A | 8/1994 | Mcintyre et al. |
| 5,336,194 A | 8/1994 | Polaschegg et al. |
| 5,336,398 A | 8/1994 | Russell et al. |
| 5,338,398 A | 8/1994 | Szwejkowski et al. |
| 5,350,360 A | 9/1994 | Ensminger et al. |
| 5,352,204 A | 10/1994 | Ensminger |
| 5,360,407 A | 11/1994 | Leonard et al. |
| 5,363,233 A | 11/1994 | Pernick |
| 5,383,233 A | 1/1995 | Russell |
| 5,383,858 A | 1/1995 | Reilly et al. |
| D355,240 S | 2/1995 | Gladfelter et al. |
| 5,387,192 A | 2/1995 | Glantz et al. |
| 5,394,457 A | 2/1995 | Leibinger et al. |
| 5,395,324 A | 3/1995 | Hinrichs et al. |
| 5,397,329 A | 3/1995 | Allen |
| 5,399,168 A | 3/1995 | Wadsworth et al. |
| 5,405,402 A | 4/1995 | Dye et al. |
| 5,417,565 A | 5/1995 | Long |
| 5,417,656 A | 5/1995 | Ensminger et al. |
| 5,421,814 A | 6/1995 | Geary |
| 5,423,334 A | 6/1995 | Jordan |
| 5,425,762 A | 6/1995 | Muller |
| 5,429,617 A | 7/1995 | Hammersmark et al. |
| 5,433,480 A | 7/1995 | Gresham et al. |
| 5,456,698 A | 10/1995 | Byland et al. |
| 5,476,460 A | 12/1995 | Montalvo |
| 5,476,880 A | 12/1995 | Cooke et al. |
| 5,484,402 A | 1/1996 | Saravia et al. |
| 5,503,630 A | 4/1996 | Ensminger et al. |
| 5,507,613 A | 4/1996 | Tokiwa |
| 5,507,813 A | 4/1996 | Dowd et al. |
| 5,509,805 A | 4/1996 | Jagmin |
| 5,513,637 A | 5/1996 | Twiss et al. |
| 5,514,103 A | 5/1996 | Srisathapat et al. |
| 5,520,632 A | 5/1996 | Leveen et al. |
| 5,527,277 A | 6/1996 | Ensminger et al. |
| 5,527,307 A | 6/1996 | Srisathapat et al. |
| 5,531,684 A | 7/1996 | Ensminger et al. |
| 5,556,381 A | 9/1996 | Ensminger et al. |
| 5,558,641 A | 9/1996 | Glantz et al. |
| 5,562,617 A | 10/1996 | Finch et al. |
| 5,562,618 A | 10/1996 | Cai et al. |
| 5,575,770 A | 11/1996 | Melsky et al. |
| 5,607,393 A | 3/1997 | Ensminger et al. |
| 5,607,407 A | 3/1997 | Tolkoff et al. |
| 5,613,945 A | 3/1997 | Cai et al. |
| 5,620,419 A | 4/1997 | Lui et al. |
| 5,632,729 A | 5/1997 | Cai et al. |
| 5,637,102 A | 6/1997 | Tolkoff et al. |
| 5,638,832 A | 6/1997 | Singer et al. |
| 5,647,855 A | 7/1997 | Trooskin |
| 5,662,600 A | 9/1997 | Watson et al. |
| 5,662,612 A | 9/1997 | Niehoff |
| 5,676,146 A | 10/1997 | Scarborough |
| 5,695,424 A | 12/1997 | Mizuta |
| 5,695,490 A | 12/1997 | Flaherty et al. |
| 5,702,128 A | 12/1997 | Maxim et al. |
| 5,702,363 A | 12/1997 | Flaherty |
| 5,704,915 A | 1/1998 | Melsky et al. |
| 5,709,668 A | 1/1998 | Wacks |
| 5,713,844 A | 2/1998 | Peyman |
| 5,713,858 A | 2/1998 | Heruth et al. |
| 5,713,859 A | 2/1998 | Finch et al. |
| 5,718,382 A | 2/1998 | Jaeger |
| 5,718,682 A | 2/1998 | Tucker |
| 5,725,507 A | 3/1998 | Petrick |
| 5,733,336 A | 3/1998 | Neuenfeldt et al. |
| 5,733,400 A | 3/1998 | Gore et al. |
| 5,741,228 A | 4/1998 | Lambrecht et al. |
| 5,743,873 A | 4/1998 | Cai et al. |
| 5,743,891 A | 4/1998 | Tolkoff et al. |
| 5,746,460 A | 5/1998 | Marohl et al. |
| 5,758,667 A | 6/1998 | Slettenmark |
| 5,769,823 A | 6/1998 | Otto |
| 5,773,552 A | 6/1998 | Hutchings et al. |
| 5,776,188 A | 7/1998 | Shepherd et al. |
| 5,792,104 A | 8/1998 | Speckman et al. |
| 5,792,116 A | 8/1998 | Berg et al. |
| 5,810,789 A | 9/1998 | Powers et al. |
| 5,824,071 A | 10/1998 | Nelson et al. |
| 5,830,172 A | 11/1998 | Leveen et al. |
| 5,833,654 A | 11/1998 | Powers et al. |
| 5,835,563 A | 11/1998 | Navab et al. |
| 5,836,935 A | 11/1998 | Ashton et al. |
| 5,840,063 A | 11/1998 | Flaherty |
| 5,843,069 A | 12/1998 | Butler et al. |
| 5,853,394 A | 12/1998 | Tolkoff et al. |
| 5,868,702 A | 2/1999 | Stevens et al. |
| 5,882,353 A | 3/1999 | Vanbeek et al. |
| 5,895,424 A | 4/1999 | Steele et al. |
| 5,906,596 A | 5/1999 | Tallarida |
| 5,908,414 A | 6/1999 | Otto et al. |
| 5,913,998 A | 6/1999 | Butler et al. |
| 5,916,263 A | 6/1999 | Goicoechea et al. |
| 5,919,160 A | 7/1999 | Sanfilippo, II |
| 5,925,017 A | 7/1999 | Kriesel et al. |
| 5,925,030 A | 7/1999 | Gross et al. |
| 5,928,197 A | 7/1999 | Niehoff |
| 5,931,829 A | 8/1999 | Burbank et al. |
| 5,935,084 A | 8/1999 | Southworth |
| 5,944,023 A | 8/1999 | Johnson et al. |
| 5,944,688 A | 8/1999 | Lois |
| 5,944,712 A | 8/1999 | Frassica et al. |
| 5,947,953 A | 9/1999 | Ash et al. |
| 5,951,512 A | 9/1999 | Dalton |
| 5,951,522 A | 9/1999 | Rosato et al. |
| 5,954,687 A | 9/1999 | Baudino |
| 5,957,890 A | 9/1999 | Mann et al. |
| 5,968,011 A | 10/1999 | Larsen et al. |
| 5,970,162 A | 10/1999 | Kawashima |
| 5,989,216 A | 11/1999 | Johnson et al. |
| 5,989,239 A | 11/1999 | Finch et al. |
| 5,997,524 A | 12/1999 | Burbank et al. |

(56) References Cited

U.S. PATENT DOCUMENTS

| | | |
|---|---|---|
| 6,007,516 A | 12/1999 | Burbank et al. |
| 6,013,051 A | 1/2000 | Nelson |
| 6,013,058 A | 1/2000 | Prosl et al. |
| 6,017,331 A | 1/2000 | Watts et al. |
| 6,022,335 A | 2/2000 | Ramadan |
| 6,033,389 A | 3/2000 | Cornish |
| 6,039,712 A | 3/2000 | Fogarty et al. |
| 6,077,756 A | 6/2000 | Lin et al. |
| 6,086,555 A | 7/2000 | Eliasen et al. |
| 6,090,066 A | 7/2000 | Schnell |
| 6,102,884 A | 8/2000 | Squitieri |
| 6,113,572 A | 9/2000 | Gailey et al. |
| 6,120,492 A | 9/2000 | Finch et al. |
| 6,161,033 A | 12/2000 | Kuhn |
| 6,171,198 B1 | 1/2001 | Lizama et al. |
| 6,171,298 B1 | 1/2001 | Matsuura et al. |
| 6,174,330 B1 | 1/2001 | Stinson |
| 6,190,352 B1 | 2/2001 | Haarala et al. |
| 6,193,684 B1 | 2/2001 | Burbank et al. |
| 6,198,807 B1 | 3/2001 | Desena |
| 6,203,570 B1 | 3/2001 | Baeke |
| 6,213,973 B1 | 4/2001 | Eliasen et al. |
| 6,228,088 B1 | 5/2001 | Miller et al. |
| 6,251,059 B1 | 6/2001 | Apple et al. |
| D445,175 S | 7/2001 | Bertheas |
| 6,269,148 B1 | 7/2001 | Jessop et al. |
| 6,287,293 B1 | 9/2001 | Jones et al. |
| 6,290,677 B1 | 9/2001 | Arai et al. |
| 6,302,875 B1 | 10/2001 | Makower et al. |
| 6,305,413 B1 | 10/2001 | Fischer et al. |
| D450,115 S | 11/2001 | Bertheas |
| 6,332,874 B1 | 12/2001 | Eliasen et al. |
| 6,347,241 B2 | 2/2002 | Burbank et al. |
| 6,355,021 B1 | 3/2002 | Nielsen et al. |
| 6,356,782 B1 | 3/2002 | Sirimanne et al. |
| 6,361,557 B1 | 3/2002 | Gittings et al. |
| 6,396,764 B1 | 5/2002 | Holland |
| 6,398,764 B1 | 6/2002 | Finch et al. |
| 6,419,680 B1 | 7/2002 | Cosman et al. |
| 6,450,937 B1 | 9/2002 | Mercereau et al. |
| 6,459,772 B1 | 10/2002 | Wiedenhoefer et al. |
| 6,471,674 B1 | 10/2002 | Emig et al. |
| 6,478,783 B1 | 11/2002 | Moorehead |
| 6,482,217 B1 | 11/2002 | Pintor et al. |
| 6,494,867 B1 | 12/2002 | Elver et al. |
| 6,497,062 B1 | 12/2002 | Koopman et al. |
| 6,500,155 B2 | 12/2002 | Sasso |
| 6,503,228 B1 | 1/2003 | Li et al. |
| 6,527,754 B1 | 3/2003 | Tallarida et al. |
| 6,537,255 B1 | 3/2003 | Raines |
| RE38,074 E | 4/2003 | Recinella et al. |
| 6,582,418 B1 | 6/2003 | Verbeek et al. |
| 6,613,002 B1 | 9/2003 | Clark et al. |
| 6,613,662 B2 | 9/2003 | Wark et al. |
| 6,626,936 B2 | 9/2003 | Stinson |
| 6,629,950 B1 | 10/2003 | Levin |
| 6,632,217 B2 | 10/2003 | Harper et al. |
| 6,652,486 B2 | 11/2003 | Bialecki et al. |
| 6,652,503 B1 | 11/2003 | Bradley |
| 6,676,633 B2 | 1/2004 | Smith et al. |
| 6,697,664 B2 | 2/2004 | Kienzle et al. |
| 6,705,316 B2 | 3/2004 | Blythe et al. |
| 6,719,721 B1 | 4/2004 | Okazaki et al. |
| 6,719,739 B2 | 4/2004 | Verbeek et al. |
| 6,738,531 B1 | 5/2004 | Funahashi |
| 6,755,842 B2 | 6/2004 | Kanner et al. |
| 6,758,841 B2 | 7/2004 | Haarala et al. |
| 6,767,356 B2 | 7/2004 | Kanner et al. |
| 6,784,783 B2 | 8/2004 | Scoggin et al. |
| 6,826,257 B2 | 11/2004 | Sayre et al. |
| 6,852,106 B2 | 2/2005 | Watson et al. |
| 6,878,136 B2 | 4/2005 | Fleury et al. |
| 6,878,137 B2 | 4/2005 | Benchetrit |
| 6,949,084 B2 | 9/2005 | Marggi et al. |
| 6,962,580 B2 | 11/2005 | Adams et al. |
| 6,994,315 B2 | 2/2006 | Ryan et al. |
| 6,997,914 B2 | 2/2006 | Smith et al. |
| 7,008,377 B2 | 3/2006 | Beane et al. |
| 7,008,412 B2 | 3/2006 | Maginot |
| 7,016,456 B2 | 3/2006 | Basu et al. |
| 7,018,361 B2 | 3/2006 | Gillespie et al. |
| 7,044,942 B2 | 5/2006 | Jolly et al. |
| 7,056,316 B1 | 6/2006 | Burbank et al. |
| 7,070,591 B2 | 7/2006 | Adams et al. |
| 7,072,704 B2 | 7/2006 | Bucholz |
| 7,074,232 B2 | 7/2006 | Kanner et al. |
| 7,076,305 B2 | 7/2006 | Imran et al. |
| 7,083,593 B2 | 8/2006 | Stultz |
| 7,108,686 B2 | 9/2006 | Burke et al. |
| 7,123,690 B1 | 10/2006 | Brown et al. |
| 7,127,040 B2 | 10/2006 | Sayre et al. |
| 7,131,962 B1 | 11/2006 | Estabrook et al. |
| 7,140,769 B2 | 11/2006 | Kay |
| 7,191,011 B2 | 3/2007 | Cantlon |
| 7,198,631 B2 | 4/2007 | Kanner et al. |
| 7,214,207 B2 | 5/2007 | Lynch et al. |
| 7,214,215 B2 | 5/2007 | Heinzerling et al. |
| 7,223,257 B2 | 5/2007 | Shubayev et al. |
| 7,229,417 B2 | 6/2007 | Foerster et al. |
| 7,235,067 B2 | 6/2007 | Morris et al. |
| D546,440 S | 7/2007 | Burnside |
| 7,242,982 B2 | 7/2007 | Singhal et al. |
| 7,252,469 B2 | 8/2007 | Zaluzec et al. |
| 7,252,649 B2 | 8/2007 | Sherry |
| 7,261,705 B2 | 8/2007 | Edoga et al. |
| D554,253 S | 10/2007 | Kornerup |
| 7,275,682 B2 | 10/2007 | Excoffier et al. |
| 7,276,075 B1 | 10/2007 | Callas et al. |
| D556,153 S | 11/2007 | Burnside |
| 7,306,579 B2 | 12/2007 | Fujii |
| 7,311,702 B2 | 12/2007 | Tallarida et al. |
| 7,318,816 B2 | 1/2008 | Bobroff et al. |
| 7,318,818 B2 | 1/2008 | Yashiro et al. |
| 7,322,953 B2 | 1/2008 | Redinger |
| D562,443 S | 2/2008 | Zinn et al. |
| 7,331,130 B2 | 2/2008 | Schweikert |
| 7,331,948 B2 | 2/2008 | Skarda |
| 7,333,013 B2 | 2/2008 | Berger |
| D564,449 S | 3/2008 | Dewberry |
| 7,347,838 B2 | 3/2008 | Kulli |
| 7,347,843 B2 | 3/2008 | Adams et al. |
| 7,351,233 B2 | 4/2008 | Parks |
| 7,377,915 B2 | 5/2008 | Rasmussen et al. |
| D574,950 S | 8/2008 | Zawacki et al. |
| 7,413,564 B2 | 8/2008 | Morris et al. |
| D578,203 S | 10/2008 | Bizup |
| 7,445,614 B2 | 11/2008 | Bunodiere et al. |
| D582,032 S | 12/2008 | Bizup et al. |
| 7,465,847 B2 | 12/2008 | Fabian |
| D595,892 S | 7/2009 | Smith et al. |
| 7,563,025 B2 | 7/2009 | Kay |
| D612,479 S | 3/2010 | Zawacki et al. |
| 7,713,251 B2 | 5/2010 | Tallarida et al. |
| 7,785,302 B2 | 8/2010 | Powers |
| 7,833,281 B2 | 11/2010 | Lehman et al. |
| 8,021,324 B2 | 9/2011 | Bizup et al. |
| 8,025,639 B2 | 9/2011 | Powers et al. |
| 8,257,325 B2 | 9/2012 | Schweikert et al. |
| 8,382,723 B2 | 2/2013 | Powers et al. |
| 8,475,417 B2 | 7/2013 | Powers et al. |
| 8,545,460 B2 | 10/2013 | Beasley et al. |
| 8,585,663 B2 | 11/2013 | Powers et al. |
| 8,603,052 B2 | 12/2013 | Powers et al. |
| 8,805,478 B2 | 8/2014 | Powers et al. |
| 9,517,329 B2 | 12/2016 | Bizup et al. |
| 9,682,186 B2 | 6/2017 | Powers et al. |
| 10,052,470 B2 | 8/2018 | Powers et al. |
| 10,179,230 B2 | 1/2019 | Powers et al. |
| 10,183,157 B2 | 1/2019 | Powers et al. |
| 10,625,065 B2 | 4/2020 | Powers et al. |
| 2001/0016717 A1 | 8/2001 | Haarala et al. |
| 2001/0051766 A1 | 12/2001 | Gazdzinski |
| 2001/0053889 A1 | 12/2001 | Marggi et al. |
| 2001/0056266 A1 | 12/2001 | Tallarida et al. |

(56) References Cited

U.S. PATENT DOCUMENTS

| | | |
|---|---|---|
| 2002/0095205 A1 | 7/2002 | Edwin et al. |
| 2002/0138068 A1 | 9/2002 | Watson et al. |
| 2002/0173769 A1 | 11/2002 | Gray et al. |
| 2003/0010929 A1 | 1/2003 | Priewe et al. |
| 2003/0028173 A1 | 2/2003 | Forsberg |
| 2003/0032918 A1 | 2/2003 | Quinn |
| 2003/0060842 A1 | 3/2003 | Chin et al. |
| 2003/0130627 A1 | 7/2003 | Smith et al. |
| 2003/0139812 A1 | 7/2003 | Garcia et al. |
| 2003/0181878 A1 | 9/2003 | Tallarida et al. |
| 2003/0191452 A1 | 10/2003 | Meglin et al. |
| 2004/0002693 A1 | 1/2004 | Bright et al. |
| 2004/0006316 A1 | 1/2004 | Patton |
| 2004/0019356 A1 | 1/2004 | Fraser et al. |
| 2004/0020462 A1 | 2/2004 | Sauler et al. |
| 2004/0044306 A1 | 3/2004 | Lynch et al. |
| 2004/0054352 A1 | 3/2004 | Adams et al. |
| 2004/0056266 A1 | 3/2004 | Suh et al. |
| 2004/0064110 A1 | 4/2004 | Forsell |
| 2004/0073196 A1 | 4/2004 | Adams et al. |
| 2004/0093069 A1 | 5/2004 | Priewe et al. |
| 2004/0106878 A1 | 6/2004 | Skujins et al. |
| 2004/0106891 A1 | 6/2004 | Langan et al. |
| 2004/0157952 A1 | 8/2004 | Soffiati et al. |
| 2004/0158207 A1 | 8/2004 | Hunn et al. |
| 2004/0167543 A1 | 8/2004 | Mazzocchi et al. |
| 2004/0176743 A1 | 9/2004 | Morris et al. |
| 2004/0181186 A1 | 9/2004 | Gellman et al. |
| 2004/0199129 A1 | 10/2004 | Dimatteo |
| 2004/0199220 A1 | 10/2004 | Cantlon |
| 2004/0204692 A1 | 10/2004 | Eliasen |
| 2004/0225254 A1 | 11/2004 | Tanaka et al. |
| 2004/0254536 A1 | 12/2004 | Conlon et al. |
| 2004/0254537 A1 | 12/2004 | Conlon et al. |
| 2005/0038390 A1 | 2/2005 | Fago et al. |
| 2005/0049553 A1 | 3/2005 | Triplett et al. |
| 2005/0070875 A1 | 3/2005 | Kulessa |
| 2005/0075614 A1 | 4/2005 | Bunodiere et al. |
| 2005/0085723 A1 | 4/2005 | Huebner |
| 2005/0113806 A1 | 5/2005 | De et al. |
| 2005/0131352 A1 | 6/2005 | Conlon et al. |
| 2005/0148866 A1 | 7/2005 | Gunderson |
| 2005/0148956 A1 | 7/2005 | Conlon et al. |
| 2005/0148957 A1 | 7/2005 | Girard et al. |
| 2005/0152841 A1 | 7/2005 | Sayre et al. |
| 2005/0171502 A1 | 8/2005 | Daly et al. |
| 2005/0182857 A1 | 8/2005 | Kong |
| 2005/0209573 A1 | 9/2005 | Brugger et al. |
| 2005/0215874 A1 | 9/2005 | Wang et al. |
| 2005/0215876 A1 | 9/2005 | Chen et al. |
| 2005/0241203 A1 | 11/2005 | Lizotte et al. |
| 2005/0256451 A1 | 11/2005 | Adams et al. |
| 2005/0256500 A1 | 11/2005 | Fujii |
| 2005/0277899 A1 | 12/2005 | Conlon et al. |
| 2005/0283119 A1 | 12/2005 | Uth et al. |
| 2006/0009788 A1 | 1/2006 | Freeman et al. |
| 2006/0017341 A1 | 1/2006 | Hahn et al. |
| 2006/0084929 A1 | 4/2006 | Eliasen |
| 2006/0089619 A1 | 4/2006 | Ginggen |
| 2006/0100592 A1 | 5/2006 | Eliasen |
| 2006/0116648 A1 | 6/2006 | Hamatake |
| 2006/0173410 A1 | 8/2006 | Moberg et al. |
| 2006/0173424 A1 | 8/2006 | Conlon |
| 2006/0178647 A1 | 8/2006 | Stats |
| 2006/0184141 A1 | 8/2006 | Smith et al. |
| 2006/0184142 A1 | 8/2006 | Schon et al. |
| 2006/0217359 A1 | 9/2006 | Wentworth et al. |
| 2006/0217659 A1 | 9/2006 | Patton |
| 2006/0224128 A1 | 10/2006 | Lurvey et al. |
| 2006/0224129 A1 | 10/2006 | Beasley et al. |
| 2006/0247584 A1 | 11/2006 | Sheetz et al. |
| 2006/0253076 A1 | 11/2006 | Butts et al. |
| 2006/0264898 A1 | 11/2006 | Beasley et al. |
| 2007/0007839 A1 | 1/2007 | Lin |
| 2007/0049876 A1 | 3/2007 | Patton |
| 2007/0055290 A1 | 3/2007 | Lober |
| 2007/0073250 A1 | 3/2007 | Schneiter |
| 2007/0078391 A1 | 4/2007 | Wortley et al. |
| 2007/0078416 A1 | 4/2007 | Eliasen |
| 2007/0078432 A1 | 4/2007 | Halseth et al. |
| 2007/0083156 A1 | 4/2007 | Muto et al. |
| 2007/0149920 A1 | 6/2007 | Michels et al. |
| 2007/0149921 A1 | 6/2007 | Michels et al. |
| 2007/0161958 A1 | 7/2007 | Glenn |
| 2007/0161985 A1 | 7/2007 | Demakas et al. |
| 2007/0179456 A1 | 8/2007 | Glenn |
| 2007/0185462 A1 | 8/2007 | Byrum |
| 2007/0191773 A1 | 8/2007 | Wojcik |
| 2007/0208313 A1 | 9/2007 | Conlon et al. |
| 2007/0219510 A1 | 9/2007 | Zinn et al. |
| 2007/0233017 A1 | 10/2007 | Zinn et al. |
| 2007/0233018 A1 | 10/2007 | Bizup et al. |
| 2007/0255234 A1 | 11/2007 | Haase et al. |
| 2007/0270691 A1 | 11/2007 | Bailey et al. |
| 2007/0270770 A1 | 11/2007 | Bizup |
| 2007/0276344 A1 | 11/2007 | Bizup et al. |
| 2007/0299408 A1 | 12/2007 | Alferness et al. |
| 2008/0004642 A1 | 1/2008 | Birk et al. |
| 2008/0008654 A1 | 1/2008 | Clarke et al. |
| 2008/0015701 A1 | 1/2008 | Garcia et al. |
| 2008/0039820 A1 | 2/2008 | Sommers et al. |
| 2008/0048855 A1 | 2/2008 | Berger |
| 2008/0108949 A1 | 5/2008 | Beasley et al. |
| 2008/0114308 A1 | 5/2008 | Di et al. |
| 2008/0138387 A1 | 6/2008 | Machiraju |
| 2008/0140025 A1 | 6/2008 | Sheetz et al. |
| 2008/0208236 A1 | 8/2008 | Hobbs et al. |
| 2008/0281279 A1 | 11/2008 | Hoendervoogt et al. |
| 2008/0319398 A1 | 12/2008 | Bizup |
| 2008/0319399 A1 | 12/2008 | Schweikert et al. |
| 2008/0319405 A1 | 12/2008 | Bizup |
| 2009/0024024 A1 | 1/2009 | Zinn |
| 2009/0024098 A1 | 1/2009 | Bizup et al. |
| 2009/0035582 A1 | 2/2009 | Nakatani et al. |
| 2009/0118683 A1 | 5/2009 | Hanson et al. |
| 2009/0156928 A1 | 6/2009 | Evans et al. |
| 2009/0171436 A1 | 7/2009 | Casanova et al. |
| 2009/0199857 A1 | 8/2009 | Peake et al. |
| 2009/0204072 A1 | 8/2009 | Amin et al. |
| 2009/0204074 A1 | 8/2009 | Powers et al. |
| 2009/0221976 A1 | 9/2009 | Linden |
| 2009/0227862 A1 | 9/2009 | Smith et al. |
| 2009/0227951 A1 | 9/2009 | Powers et al. |
| 2010/0004735 A1 | 1/2010 | Yang et al. |
| 2010/0042073 A1 | 2/2010 | Oster et al. |
| 2010/0069743 A1 | 3/2010 | Sheetz et al. |
| 2011/0054312 A1 | 3/2011 | Bell et al. |
| 2019/0134373 A1 | 5/2019 | Barron et al. |
| 2019/0151641 A1 | 5/2019 | Powers et al. |
| 2019/0217073 A1 | 7/2019 | Maniar et al. |
| 2019/0252603 A1 | 8/2019 | Wiley et al. |
| 2019/0275311 A1 | 9/2019 | Hibdon et al. |
| 2020/0086105 A1 | 3/2020 | Powers et al. |

FOREIGN PATENT DOCUMENTS

| | | | |
|---|---|---|---|
| DE | 8437873 | U1 | 3/1986 |
| DE | 3447202 | A1 | 7/1986 |
| DE | 19745654 | A1 | 4/1999 |
| EP | 0619101 | A1 | 10/1994 |
| EP | 0750520 | B1 | 8/2000 |
| EP | 1238682 | A2 | 9/2002 |
| EP | 2081634 | A1 | 7/2009 |
| EP | 1896117 | B1 | 1/2011 |
| EP | 3275503 | A1 | 1/2018 |
| EP | 3311877 | A1 | 4/2018 |
| FR | 1509165 | A | 1/1968 |
| FR | 2569987 | A1 | 3/1986 |
| FR | 2586569 | A1 | 3/1987 |
| GB | 2203342 | A | 10/1988 |
| JP | 2500388 | Y2 | 6/1996 |
| JP | H08168322 | A | 7/1996 |
| JP | 2602109 | B2 | 4/1997 |
| JP | 2003102831 | A | 4/2003 |

(56) References Cited

FOREIGN PATENT DOCUMENTS

| | | |
|---|---|---|
| JP | 2004350937 A | 12/2004 |
| JP | 2006500087 A | 1/2006 |
| JP | 2006025948 A | 2/2006 |
| JP | 2008168322 A | 7/2008 |
| MX | 2009004190 A | 4/2009 |
| MX | 2010000703 A | 7/2010 |
| WO | 8600213 A1 | 1/1986 |
| WO | 9305730 A1 | 4/1993 |
| WO | 9514504 A1 | 6/1995 |
| WO | 9701370 A1 | 1/1997 |
| WO | 9706845 A1 | 2/1997 |
| WO | 9711726 A1 | 4/1997 |
| WO | 9817337 A1 | 4/1998 |
| WO | 9942166 A1 | 8/1999 |
| WO | 0004800 A1 | 2/2000 |
| WO | 0011726 A1 | 3/2000 |
| WO | 0014504 A1 | 3/2000 |
| WO | 0017337 A1 | 3/2000 |
| WO | 0033901 A1 | 6/2000 |
| WO | 0047264 A1 | 8/2000 |
| WO | 0047549 A1 | 8/2000 |
| WO | 0100480 A1 | 1/2001 |
| WO | 0247549 A1 | 6/2002 |
| WO | 02100480 A2 | 12/2002 |
| WO | 03037215 A2 | 5/2003 |
| WO | 03086508 A1 | 10/2003 |
| WO | 2004004800 A2 | 1/2004 |
| WO | 2004071555 A2 | 8/2004 |
| WO | 2004091434 A2 | 10/2004 |
| WO | 2005037055 A2 | 4/2005 |
| WO | 2006078915 A2 | 7/2006 |
| WO | 2006096686 A1 | 9/2006 |
| WO | 2006116438 A2 | 11/2006 |
| WO | 2006130133 A1 | 12/2006 |
| WO | 2006134100 A1 | 12/2006 |
| WO | 2007/025266 | 3/2007 |
| WO | 2006116438 A3 | 3/2007 |
| WO | 2007079024 A2 | 7/2007 |
| WO | 2007092210 A1 | 8/2007 |
| WO | 2007094898 A2 | 8/2007 |
| WO | 2006078915 A3 | 9/2007 |
| WO | 2007098771 A2 | 9/2007 |
| WO | 2007109164 A2 | 9/2007 |
| WO | 2007126645 A2 | 11/2007 |
| WO | 2007136538 A2 | 11/2007 |
| WO | 2008008126 A2 | 1/2008 |
| WO | 2008019236 A1 | 2/2008 |
| WO | 2008048361 A1 | 4/2008 |
| WO | 2008063226 A2 | 5/2008 |
| WO | 2008147760 A1 | 12/2008 |
| WO | 2008157763 A1 | 12/2008 |
| WO | 2009002839 A1 | 12/2008 |
| WO | 2009012385 A1 | 1/2009 |
| WO | 2009012395 A1 | 1/2009 |
| WO | 2009035582 A1 | 3/2009 |
| WO | 2009046439 A2 | 4/2009 |
| WO | 2009046725 A1 | 4/2009 |
| WO | 2009108669 A1 | 9/2009 |

OTHER PUBLICATIONS

Bard Access System Product Drawings Representative of the Bard Access System Products on the Market on or Around Mar. 1995, as Indicated by the Bard Access Systems 1995 Product Release to Market form for "M.R.I. Port with8 Fr. ChronoFiex Catheter," "M.R.I. Port with 8 Fr. ChronoFiex Catheter with Intro-EzeTM,", "M.R.I. Port with 8 Fr. Chrono-Flex Catheter and Peel Apart," "M.R.I. Port with 8 Fr. ChronoFiex Catheter Demo Kit,", Mar. 21, 1995, 6 pages.
Declaration of Kelly Christian, Director of Product Development at Bard Access Systems, Inc, in Support of and Depicting a Product on the Market by Quinton Company Approximately Ten Years Prior to Oct. 22, 2009, 1 page.
Extravasation of Radiologic Contrast, PA-PSRS Patient Safety Advisory—vol. 1, No. 3, Sep. 2004, 6 pages.
Extreme Access, Bard Access Systems, Inc., Product Brochure, 2003, 5 pages.
Guidance for Industry and FDA Staff, Use of Symbols on Labels and in Labeling of In Vitro Diagnostic Devices Intended for Professional Use, Nov. 30, 2004, 12 pages.
Guidance for Institutional Review Boards and Clinical Investigators 1998 Update: Medical Devices, U.S. Food and Drug Administration,Version Sep. 10, 2008, 13 pages.
Guidance on Medical Device Patient Labeling; Final Guidance for Industry and FDA Reviewers, Apr. 19, 2001, 54 pages.
International Preliminary Report on Patentability and Written Opinion Received for PCT Patent Application No. PCT/US2006/049007, dated Jul. 1, 2008, 5 pages.
International Preliminary Report on Patentability and Written Opinion Received for PCT Patent Application No. PCT/US2006/008022, dated Sep. 12, 2007, 6 pages.
International Search Report and Written Opinion for PCT Patent Application No. PCT/US2008/078976 , dated Apr. 3, 2009, 6 pages.
International Search Report and Written Opinion received for PCT Patent Application No. PCT/US08/067679, dated Sep. 30, 2008, 7 pages.
International Search Report and Written Opinion Received for PCT Patent Application No. PCT/US2008/070330, dated Dec. 1, 2008, 10 pages.
International Search Report Received for PCT Patent Application No. PCT/US06/008022, dated Jul. 5, 2006, 2 pages.
International Search Report Received for PCT Patent Application No. PCT/US06/015695, dated Jan. 11, 2007, 6 pages.
IsoMed Constant-Flow Infusion System (Year: 2000), 111 pages.
Product Specifications, Port-A-Cath P.A.S. Port Systems by Deltec, 1999, 2 pages.
Reminders form FDA Regarding Ruptured Vascular Access Devices from Power Injection, Jul. 2004, 2 pages.
Signs, Symbols, and Icons: Pre-history to the Computer Age, author: Rosemary Sassoon and Albertine Gaur, first published in 1997, 3 pages.
Title User Manual Sprint, Available at http://www.cochlearamericas.com/PDFs/UserManualSprint.pdf, Dec. 1, 2012, 2 Pages.
User Manual for the ESPrit 3G Apeech Processor and Accessories, Nucleus Cochlear Implant Systems; available at <http://www.cochlearamericas.com/PDFs/UserManualSprint.pdf>, Issue 2, Dec. 2001, 2 pages.
Implantable Port Device, U.S. Patent Application filed Sep. 7, 2007, 8 pages.
Bard Access Systems, Inc., "Hickman Subcutaneous Ports & Hickman/Broviac Catheters", Bard Exhibit, vol. 1017, Jan. 1, 1992.
Bard Access Systems, Inc., "Ports—Setting the Standard with a Comprehensive Family of Ports", Bard Exhibit vol. 1002, Jan. 1, 2003, pp. 1-17.
Bard Access Systems, Inc., "Power Port—Implantable Port—Feel the New Standard of Care—Guidelines for CT Technologists", Bard Exhibit 1004, C.R. Bard, Inc., Feb. 1, 2007, 1 Page.
Biffi et al., A Randomized, Prospective Trial of Central Venous Ports Connected to Standard Open-Ended or Groshong Catheters in Adult Oncology Patients, American Cancer Society vol. 92, No. 5, Sep. 1, 2001, pp. 1204-1212.
Biffi et al., Best Choice of Central Venous Insertion Site for the Prevention of Catheter-Related Complications in Adult Patients Who Need Cancer Therapy: A Randomized Trial, Annals of Oncology, 6 Pages.
Biffi et al., Use of Totally Implantable Central Venous Access Ports for High-Dose Chemotherapy and Peripheral Blood Stem Cell Transplantation: Results of a Monocentre Series of 376 Patients, Annals of Oncology vol. 5, Jan. 1, 2004, pp. 296-300.
Biffi, et al., Best Choice of Central Venous Insertion Site for the Prevention of Catheter-Related Complications in Adult Patients Who Need Cancer Therapy: A Randomized Trial., Annals of Oncology, Jan. 29, 2009, 6 pages.
Bioenterics® Lap-Band®, Adjustable Gastric Banding System, by Inamed Health, Product Brochure, Dec. 1, 2003, 22 pages.

(56) References Cited

OTHER PUBLICATIONS

Carlson et al., Safety Considerations in the Power Injection of Contrast Media via Central Venous Catheters During Computed Tomographic Examinations, Investigative Radiology, vol. 27, No. 5, May 1992, pp. 337-340.
Costa et al., Understanding Contrast Media, Journal of Infusion Nursing, vol. 27, No. 5, Sep./Oct. 2004, 11 pages.
Costa, Nancy, More Than Skin Deep: An Overview of Iodinated Contrast Media, Journal for the Association for Vascular Access, vol. 8, No. 4, 2003, 6 pages.
Coyle et al., Power Injection of Contrast Media via Peripherally Inserted Central Catheters for CT, The Journal of the Association for Vascular Access (JAVA), vol. 15, No. 8, Aug. 2004, pp. 809-814.
Extended European Search Report received for EP Application No. EP 08781983.5, 5 pages.
Fallscheer et al., Injury to the Upper Extremity Caused by Extravasation of Contrast Medium Medium: A, Scandinavian Journal of Plastic and Reconstructive Surgery and Hand Surgery, vol. 41, pp. 26-32, 2007, 7 pages.
Herts et al., Power Injection of Contrast Media Using Central Venous Catheters: Feasibility, Safety and Efficacy, AJR:176(2), Feb. 2001, pp. 447-453.
Herts et al., Power Injection of Intravenous Contrast Material Through Central Venous Catheters for CT: In Vitro Evaluation, Radiology, vol. 200, No. 3, Sep. 1996, pp. 731-735.
Hou et al., Comparisons of Outcomes and Survivals for Two Central Venous Access Port Systems, Journal of Surgical Oncology, vol. 91, Jan. 1, 2005, pp. 61-66.
I Named Health, Adjustable Gastric Banding System, Product Brochure, BioEnterics® Lap-Band®, Dec. 2003, 22 pages.
Johnson Kathleena., Power Injectable Portal Systems, Journal of Radiology Nursing, vol. 28, Issue 1, Mar. 2009, 6 pages.
Lamaitre Vascular, Port Implantations: using the OptiLock Implantable Port, product information, available at <http://www.lemaitre.com/specs_pop.asp>, Apr. 2003, 14 pages.
Lap-Band APTM, System with Adjustable Gastric Banding system with Omniform Design, Product Brochure, Jul. 2007, 16 pages.
Lap-Band®, System Fact Sheet, Allergan, Inc., 2007, 2 pages.
Medcomp, PortCT Technology, Display at SIR Conference, Toronto, Canada, Mar. 2006, 1 page.
Extended European Search Report received for European Patent Application No. 17189436.3 , dated Oct. 13, 2017.
International Search Report and Written Opinion received for PCT Patent Application No. PCT/US2007/006776, dated Dec. 18, 2007, 3 pages.
International Search Report and Written Opinion received for PCT Patent Application No. PCT/US2007/006776, dated Jan. 2, 2009, 6 pages.
International Search Report Received for PCT Patent Application No. PCT/US1999/028695, dated Apr. 11, 2000, 2 pages.
International Search Report Received for PCT Patent Application No. PCT/US2009/062854, dated Dec. 23, 2009, 2 pages.
International Search Report and Written Opinion Received for PCT Patent Application No. PCT/US06/49007, dated Oct. 1, 2007, 6 pages.
International Search Report and Written Opinion Received for PCT Patent Application No. PCT/US07/006776, dated Dec. 18, 2007, 4 pages.
International Search Report and Written Opinion Received for PCT Patent Application No. PCT/US08/070345, dated Dec. 1, 2008, 11 pages.
International Search Report Received for PCT Patent Application No. PCT/US2006/008022, dated Jul. 5, 2006, 2 pages.
International Search Report and Written Opinion Received for PCT Patent Application No. PCT/US2006/015695, dated Jan. 11, 2007, 8 pages.
International Preliminary Report on Patentability and Written Opinion Received for PCT Patent Application No. PCT/US2006/016056, dated Oct. 30, 2007, 9 pages.
International Search Report and Written Opinion Received for PCT Patent Application No. PCT/US2006/49007, dated Oct. 1, 2007, 6 pages.
International Preliminary Report on Patentability and Written Opinion Received for PCT Patent Application No. PCT/US2007/006776, 3 pages.
International Preliminary Report on Patentability Received for PCT Application No. PCT/US2007/011015, dated Nov. 23, 2009, 9 pages.
International Search Report and Written Opinion Received for PCT Patent Application No. PCT/US2007/011015, dated Jun. 10, 2008, 5 pages.
International Search Report and Written Opinion Received for PCT Patent Application No. PCT/US2007/011456, dated Aug. 28, 2008, 6 pages.
International Search Report and Written Opinion Received for PCT Patent Application No. PCT/US2008/010520, dated Feb. 24, 2009, 6 pages.
International Search Report and Written Opinion Received for PCT Patent Application No. PCT/US2008/067679, dated Sep. 30, 2008, 7 pages.
International Search Report and Written Opinion Received for PCT Patent Application No. PCT/US2008/070345, dated Dec. 1, 2008, 11 pages.
International Search Report Received for PCT Application No. PCT/US2009/062854, dated Dec. 23, 2009, 2 pages.
Plinski et al., Implantable Cardioverter-Defribillators: Implications for the Nonelectrophysiologist, Annals of Internal Medicine, Abstract of vol. 122, No. 10, pp. 770-777.
Port-a-Cath®, Implantable Epidural, Aterial and Peritonial Access Systems, Internet Product Listing of Nov. 19, 2000, available at <http://web. archive.org/web/20001119035900/www.deltec.com/cPacspl.htm,>, Oct. 17, 2009, 2 pages.
Port-a-Cath®, Many Port-a-Cath® System Choices, Product Brochure, SIMS Deltec, Inc., 1996, 5 pages.
Port-a-Cath®, Single-lumen Implantable Vascular Access Systems, Product Specifications Smith Medical, 2004, 4 pages.
Rappolt et al., Radiopaque Codification and X-ray Identification of Ingested Drugs, Ingestive Radioiogy, May-Jun. 1966, 4 pages.
Salis et al., Maximal Flow Rates Possible During Power Injection Through Currently Available PICCs: An In-Vitro Study, Journal of the Association for Vascular Access, vol. 15, No. 3, Mar. 2004, pp. 275-281.
Sandstede Joern, Pediatric CT, Available online at www.multislice-ct.com, MultiSLICE-CT.com, version 02, May 2, 2003, 36 pages.
Sanelli et al., "Safety and Feasibility of Using a Central Venous Catheter for Rapid Contrast Injection Rates", American Journal of Radiology, vol. 183, Dec. 2004, pp. 1829-1834.
Sawyer Dick, Do It by Design: An Introduction to Human Factors in Medical Devices, U.S. Department of Health and Human Services, Public Health Service, Food and Drug Administration, Center for Devices and Radiological Health, Dec. 1996, 55 pages.
Shah Tilak M., Radiopaque Polymer Formulations for Medical Devices, Medical Device and Diagnostic Industry, Mar. 2000, 6 pages.
Smith Lisa Hartkoph, Implanted Ports, Computer Tomography, Power Injectors, and Catheter Rupture, Clinical Journal of Oncology Nursing, vol. 12, No. 5, Oct. 2008, 4 pages.
Solomon et al., CIN Strategies: Anticipate, Manage, Prevent, Supplement to Imaging Economics, May 1, 2007, 20 Pages.
Steinbach et al., Breast Implants, Common Complications, and Concurrent Breast Disease, RadioGraphies, vol. 13, No. 1, Jan. 1, 1993, pp. 95-118.
Stevens et al., A Randomized, Prospective Trial of Conventional Vascular Ports vs. The Vortex "Clear-Flow" Reservoir Port in Adult Oncology Patients, The Journal of Vascular Access Devices, 2000, pp. 37-40.
Sullivan et al., Radiopaque Markers on Mammary Implants, American Journal of Roentgenology vol. 153(2):428, Aug. 1989, 2 pages.
Teichgraber et al., Central Venous Access Catheters: Radiological Management of Complications, Cardiovascular and Interventional Radiology, Review Article, Jul. 31, 2003, 13 pages.

(56) References Cited

OTHER PUBLICATIONS

Thistlethwaite et al., Generalized Feature-Based RSA of Orthopaedic Implants, Summer Bioengineering Conference Sonesta Beach Resort in Key Biscayne, Florida, Jun. 25-29, 2 pages.
Extended European Search Report Received for European Patent Application No. 07753408.9, dated Aug. 24, 2012.
International Preliminary Report on Patentability and Writen Opinion Received for PCT Patent Application No. PCT/US2006/016056, dated Oct. 30, 2007, 9 pages.
International Preliminary Report on Patentability and Written Opinion received for PCT Patent Application No. PCT/US2006/015695, dated Oct. 30, 2007,9 pages.
International Preliminary Report on Patentability received for PCT Patent Application No. PCT/US2007/006776, completed on Nov. 16, 2008, 3 pages.
International Preliminary Report on Patentability received for PCT Patent Application No. PCT/US2007/006776 , dated Mar. 6, 2008, 3 pages.
Urquiola et al., Using Lead Foil as a Radiopaque Marker for Computerized Tomography Imaging When Implant Treatment Planning, The Journal of Prosthetic Dentistry, vol. 77, No. 2, 1997, pp. 227-228.
International Search Report and Written Opinion received for International Patent Application No. PCT/US2012/050586, dated Oct. 22, 2012.
Vergara et al., Adverse Reactions to Contrast Media in CT: Effects of Temperature and Ionic Property, Radiology, vol. 199, No. 2, May 1, 1996, 4 pages.
Vogelzang Robertl., "Power Injection Through Central Venous Catheters: Physiological and Hemodynamic Considerations", The McGaw Medical Center of Northwestern University, Feinberg School of Medicine, 3 pages.
Wells S, Venous Access in Oncology and Haematology Patients: Part One, Nursing Standard, vol. 22, No. 52, pp. 39-46,, Sep. 3, 2008, 9 pages.
Williamson et al., Assessing the Adequacy of Peripherally Inserted Central Catheters for Power Injection of Intravenous Contrast Agents for CT, Journal of Computer Assisted Tomography, vol. 6, No. 6, 2001, pp. 932-937.
Funaki, "Central Venous Access: A Primer for the Diagnostic Radiologist", 2002, AJR, 179:309-318.
Cope et al., Access Device Guidelines—Recommendations for Nursing Practice and Education, 2d Edition, 2004, 85 pages.
Gebauer et al., "Contrast Media Power Injection Using Central-Venous Port Catheters—Results of an In Vitro Study", Experimental Radiology, 2005, 177:1417-1423.
"Radiopaque Imprinting Enables Alternative to Angioplasty", Medical Product Manufacturing News, Apr. 2003, 1 page.
McKillop et al., "Retained Surgical Swab Misinterpreted as Epicardial Pacing Wire on Chest X Ray", 1996, Heart, 75:342.
Wolfson et al., "Imaging of Surgical Paraphernalia: What Belongs in the Patient and What Does Not", 2000, Radiographics, 20:1665-1673.
O'Connor et al., "Imaging of Retained Surgical Sponges in the Abdomen and Pelvis", 2003, AJR, 180:481-489.
Walter et al., "Radiographic Identification of Commonly Used Implanted Pacemakers", The New England Journal of Medicine, 1969, vol. 281, 22:1230-1231.
Walter, "Radiographic Identification of Commonly Used Pulse Generators-1970", 1971, JAMA, vol. 215, 12:1974-1975.
U.S. Appl. No. 60/658,518, filed Mar. 4, 2005, 62 pages.
The extended European search report, dated Mar. 3, 2018, for EP App. No. 17193828.5, which claims priority to U.S. Appl. No. 60/961,133, filed Jul. 19, 2007, 8 pages.
Declaration of Annemarie Boswell, dated Jul. 23, 2005, including Attachment A: Powerport Guidelines for CT Technologists, copyright 2007 Revised date Feb. 2007, 8 pages.
Interference Decision, Zinn vs Powers, Patent Interference No. 105,860, Paper 50, Sep. 11, 2012, 9 pages.

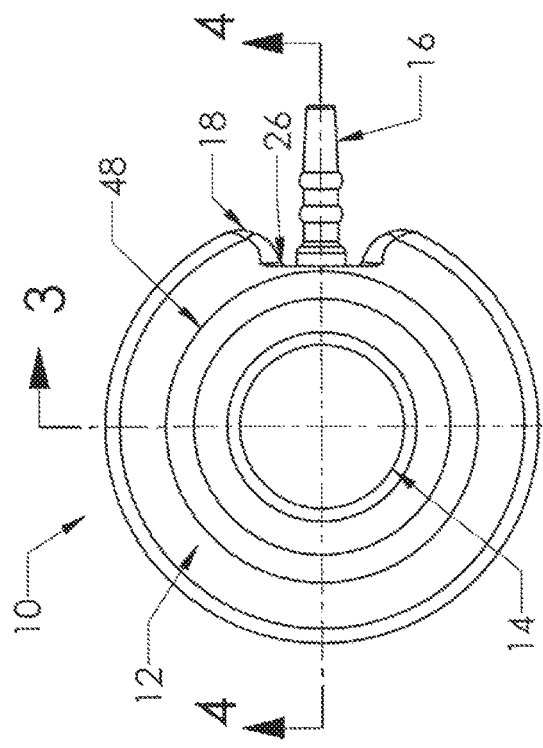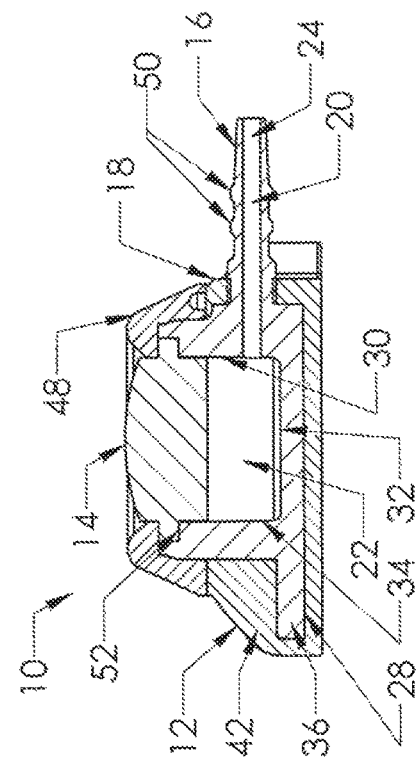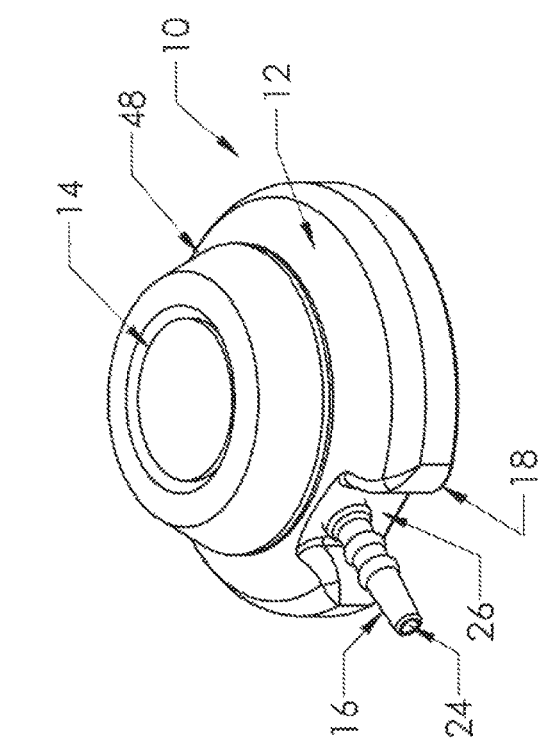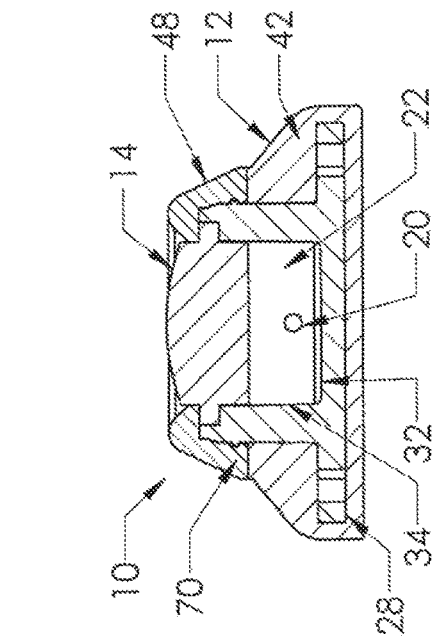

VENOUS ACCESS PORT ASSEMBLY WITH X-RAY DISCERNABLE INDICIA

CROSS-REFERENCE TO RELATED APPLICATIONS

This application is a continuation of U.S. patent application Ser. No. 15/251,122, filed Aug. 30, 2016, which is a continuation of Ser. No. 13/088,762, filed Apr. 18, 2011 (now U.S. Pat. No. 9,517,329, issued Dec. 13, 2016), which is a continuation of U.S. patent application Ser. No. 12/175,182, filed Jul. 17, 2008 (now U.S. Pat. No. 8,021,324, issued Sep. 20, 2011), which claims the benefit of U.S. Provisional Application Ser. No. 60/961,133, filed Jul. 19, 2007, and a continuation-in-part of U.S. patent application Ser. No. 11/725,287, filed Mar. 19, 2007, which claims the benefit of U.S. Provisional Application Ser. No. 60/852,591, filed Oct. 18, 2006, the contents of all said applications are incorporated herein by reference.

FIELD OF THE INVENTION

This relates to the field of medical devices and more particularly to venous access ports for the infusion of fluids into a patient and/or withdrawal of fluids from a patient.

BACKGROUND OF THE INVENTION

Venous access ports for the infusion and/or withdrawal of fluids from a patient are well-known, secured to the proximal end of an implanted catheter. These ports are typically used for drug infusion or for withdrawal of small amounts of blood, where large flows of fluid are not required. The ports are assemblies of a needle-impenetrable housing with a discharge port in fluid communication with a catheter and a reservoir within the port housing, and provide a subcutaneous self-sealing septum that defines an access site for multiple needle sticks through the covering skin tissue of the patient, through the septum, and into the reservoir, without the need to continuously search for new access sites. Examples of such ports are disclosed, for example, in U.S. Pat. Nos. 4,704,103; 4,762,517; 4,778,452; 5,185,003; 5,213,574 and 5,637,102.

It is desired to provide a venous access port assembly that provides for a radiologist, radiology technologist, nurse, and ultimately a medical practitioner to be able to discern an important property of the port assembly after the port assembly has been implanted into a patient.

SUMMARY OF THE INVENTION

An embodiment of the present invention is related to a venous access port having a housing and a septum, providing an interior reservoir and a passageway extending from the reservoir through a stem of a discharge port to establish fluid communication with a proximal end of a catheter lumen to which the port assembly is secured prior to placement of the assembly into a patient. The port may optionally have more than one reservoir and associated septum. An embodiment of the present invention includes the incorporation of X-ray discernable indicia onto a venous access port that is discernible under X-ray examination to provide information concerning the nature or key attribute of the venous access port, so that the practitioner, subsequent to the date of implantation thereof, can determine that nature or key attribute under X-ray examination. One such key attribute in particular would be for example that the venous access port is rated to be used for power injection such as of contrast fluid, wherein for example the letters "CT" (for "computed tomography", or "contrast enhanced computed tomography") would be provided that are of radiopaque material, or are cutouts through radiopaque material. The attribute in this example is the property of the port being adapted to withstand high pressures that are used for injection of contrast fluid into a patient, and the letters "CT" would be understood in medical practice to indicate that the port is suitable for the high pressure injection of contrast fluid.

In one embodiment, a disc of radiopaque material includes cutouts of letters "CT" (although other indicia may be utilized) through the body of the disc. In another embodiment, discrete letters "CT" (although other indicia may be utilized) are provided of radiopaque material. With either embodiment, the disc or letters may be insert molded within the housing base bottom wall, or they may be affixed to the bottom surface of the housing base, preferably within complementary recesses thereinto, in such a manner that the letters "CT" are readable from above the port assembly in an X-ray.

BRIEF DESCRIPTION OF THE DRAWINGS

The accompanying drawings, which are incorporated herein and constitute part of this specification, illustrate embodiments of the invention, and, together with the general description given above and the detailed description given below, serve to explain the features of the embodiments of the invention. In the drawings:

FIGS. 1 and 2 are an isometric view and a plan view of a venous access port, in accordance with an exemplary embodiment of the present invention;

FIGS. 3 and 4 are cross-sectional views of the port of FIGS. 1 and 2 taken along lines 3-3 and lines 4-4 of FIG. 1, respectively;

DETAILED DESCRIPTION OF THE INVENTION

Figure 5:
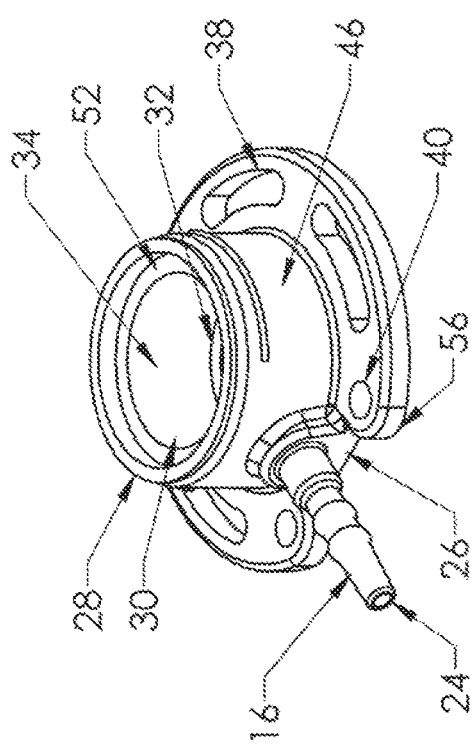
FIG. 5 is an isometric view of the needle-impenetrable housing base of the venous access port of FIG. 1.

Certain terminology is used herein for convenience only and is not to be taken as a limitation on the present invention. The terms "distal" and "proximal" refer, respectively, to directions closer to and away from the insertion tip of a catheter in an implantable catheter assembly. The terminology includes the words specifically mentioned, derivatives thereof, and words of similar import. The embodiments illustrated below are not intended to be exhaustive or to limit the invention to the precise form disclosed. These embodiments are chosen and described to best explain the principle of the invention and its application and practical use and to enable others skilled in the art to best utilize the invention.

Venous access port assembly 10 of FIGS. 1 to 4 includes a housing 12 and a septum 14, with a discharge port 16 extending from a distal end 18 of the port assembly 10 to be attached securely and sealingly to the proximal end of a catheter (not shown). A passageway 20 extends from the interior reservoir 22 to the distal tip opening 24 of discharge port 16. A recess 26 is seen to be provided along both sides of discharge port 16, facilitating insertion of the discharge port 16 into the catheter lumen and providing a clearance for a locking sleeve or clamp (not shown) utilized to compress the catheter lumen wall against the exterior surface of the discharge port 16 for assured sealed connection of the catheter with the port assembly 10.

With reference now to FIGS. 3 to 7, the interior of the port assembly 10 is shown to provide an interior reservoir 22. Housing 12 is shown to include a housing base 28 of needle-impenetrable material that includes a well 30 having a bottom floor 32 and side walls 34 that define the interior reservoir 22 beneath septum 14. Bottom floor 32 may be convex or elevated (not shown) toward the center of the reservoir, if desired. Housing base 28 includes a base flange 36 extending radially outwardly from the bottom of well 30, and base flange 36 includes openings 38,40 that serve to enable suturing to the patient upon placement of the venous access port and the attached catheter into the patient.

As shown in FIGS. 3 and 4, a skirt 42 is overmolded about housing base 28 and may be of silicone elastomer. It is seen that skirt 42 encapsulates the outer surfaces of the bottom wall 44 and the bottom portion of the side walls 46 of housing base 28, and is shown to fill in the suture holes 38,40; but since the material is silicone elastomer, suturing is possible since the suturing needle can easily be inserted through the material of skirt 42 and through the suture holes, and thereafter the filled openings provide minimal opportunity for ingrowth of patient tissue into the openings.

Figure 7:
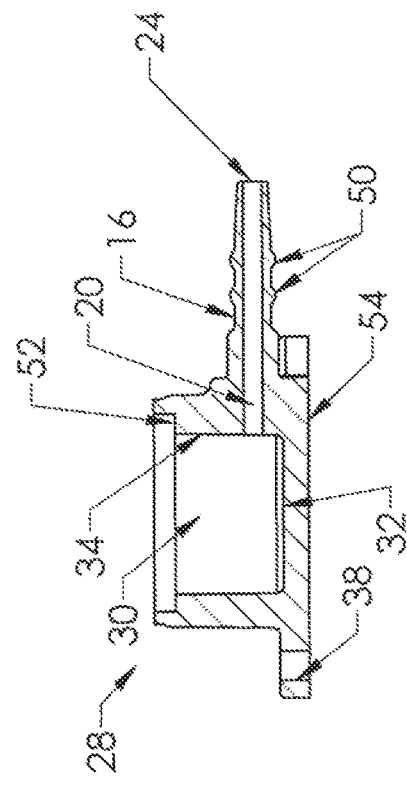
FIGS. 6 and 7 are transverse cross-sectional and longitudinal cross-sectional views of the housing base of FIG. 5.
Figure 6:
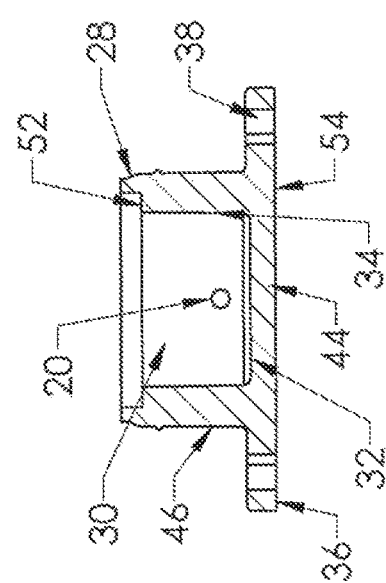

Also seen in FIGS. 1 to 4 is cap 48, which secures to housing base 28 to in turn secure septum 14 in position in the port assembly 10. Preferably, skirt 42 is insert molded onto base flange 36 of housing base 28 before cap 48 is secured to the upper portion of housing base 28 to secure the septum in position. It is seen in FIGS. 4 and 7 that discharge port 16 is integral with housing base 28 as is preferable. Discharge port 16 is shown to have a pair of annular ridges 50 that facilitate with the mechanical connection of the catheter proximal end with the port assembly 10. Housing base 28 includes a septum seat 52 extending into the top of well 30, into which a flange of the septum will be seated, preferably under radially inward compression. Housing base 28 has a bottom outer surface 54.

Figure 8:
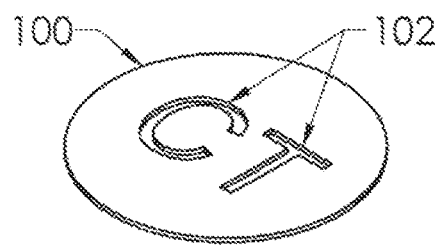
FIG. 8 is an isometric view of a first embodiment of X-ray discernable indicia, being a disc of radiopaque material having letters cut out thereof.
Figure 9:
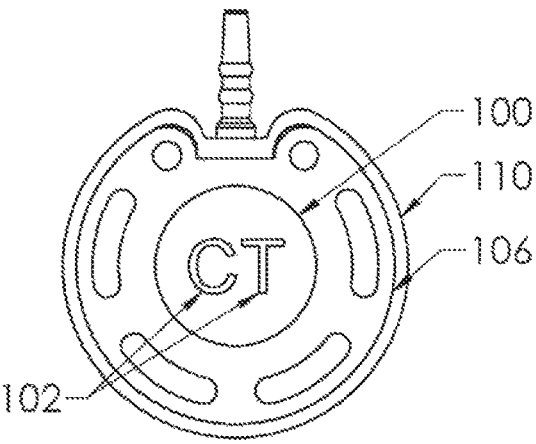
FIGS. 9 to 11 are bottom, cross-sectional, and top views of the port assembly of FIGS. 1 to 7 having the disc of FIG. 8 affixed to the housing base of FIGS. 6 and 7 and within a shallow recess into its bottom surface, with silicone covering molded thereover, and the indicia being shown in dashed lines in FIGS. 9 and 11.
Figure 10:
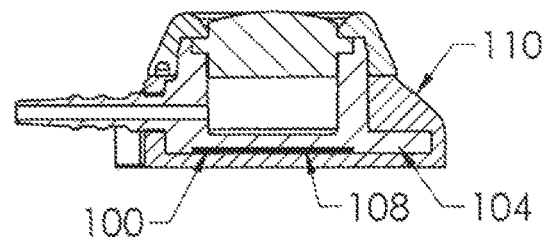

FIG. 8 shows a first embodiment of a component of radiopaque material of the present invention in the form of a disc 100, such as of titanium. Cutouts 102 are formed through the disc body, shown in FIG. 8 as the alphabetical letters "CT". Disc 100 is affixed to the bottom surface 104 of housing base 106 in FIGS. 9 and 10, preferably within a complementary shallow recess 108 thereinto. A skirt 110 of silicone material is molded over the housing base, and is transparent so that the letters "CT" are visible from below but in a mirror-image orientation on the bottom outer surface of the housing base (FIG. 9) so that the indicia would appear as "CT" when the X-ray is viewed (FIG. 11), easily discerned by the radiologist or technologist. Centering of the indicia within the region directly beneath the reservoir and septum minimizes any obscuring by the structure of the venous access port assembly, and the indicia may also be easily discernable should the port assembly be at an angle from the horizontal plane of the X-ray.

Figure 11:
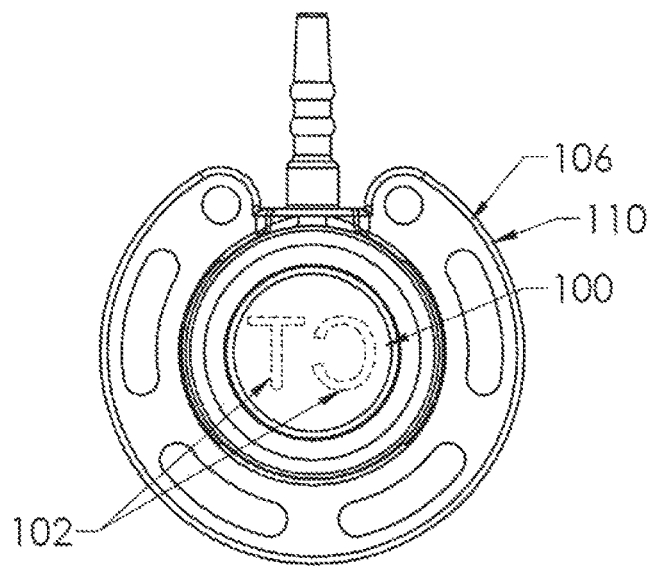
Figure 12:
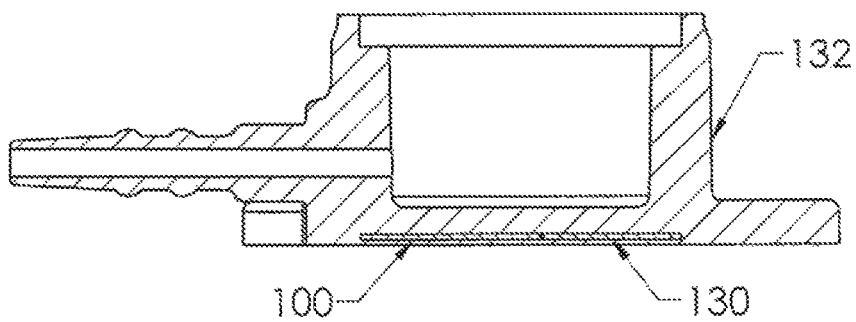
FIG. 12 is a cross-sectional view of an alternate embodiment of the housing base having the disc of FIG. 8 insert molded embedded within the bottom wall of the base.

In FIG. 12, an alternate embodiment of the present invention is shown, in which the disc 100 of FIG. 8 is embedded within the thickness of the bottom wall 130 of the housing base 132, and the X-ray would appear very similar to that shown in FIG. 11 but the indicia would not be visible from below the housing base or the port assembly.

Figure 13:
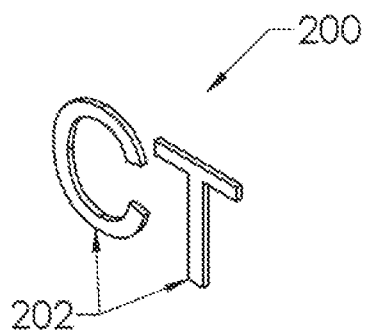
FIG. 13 is an isometric view of a second embodiment of radiopaque indicia, comprising a set of discrete letters of radiopaque material.
Figure 14:
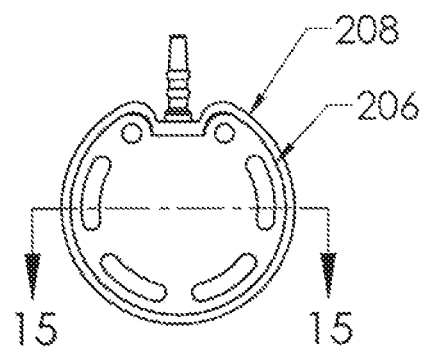
FIGS. 14 and 15 are a bottom view and a cross-sectional view of a port assembly of FIGS. 1 to 7 having the discrete letters of FIG. 13 insert molded into the bottom wall of the housing base, with FIG. 15 taken along lines 15-15 of FIG. 13.
Figure 16:
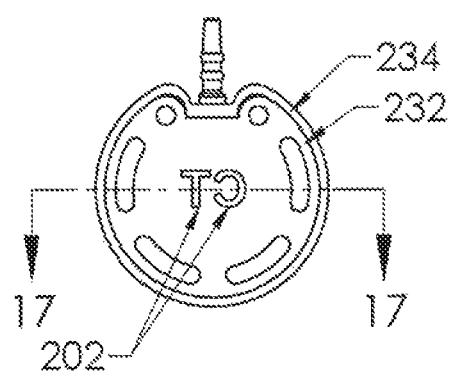
FIGS. 16 to 18 are a bottom view, cross-sectional view, and an isometric bottom view of a port assembly of FIGS. 1 to 7 having the discrete letters of FIG. 13 affixed to the bottom surface of the housing base, shown within respective recesses thereinto, with a silicone covering molded thereover, with FIG. 17 taken along lines 17-17 of FIG. 16.
Figure 15:
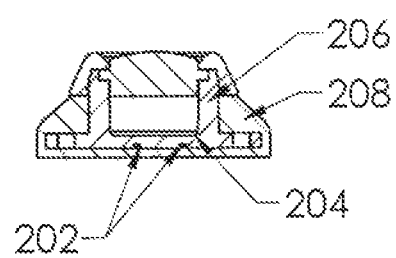
Figure 17:
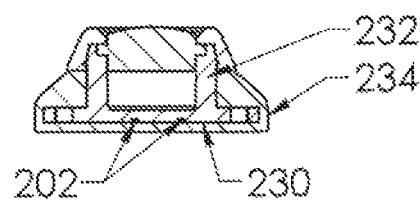
Figure 18:
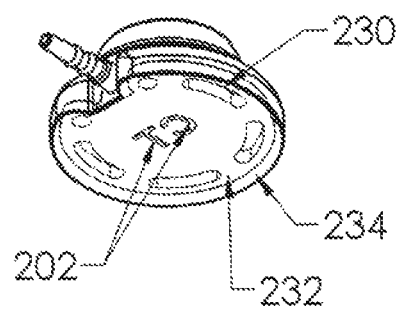

A second embodiment of X-ray discernable indicia 200 is shown in FIG. 13, and is utilized in the port assemblies of FIGS. 14 to 18. In FIG. 13, the indicia comprise a set of discrete indicia elements 202 of radiopaque material, such as being stamped from a sheet of titanium. Again, as is preferred, the indicia comprise the alphabetical letters "C" and "T" and are utilized together as a set. In FIGS. 14 and 15, the discrete elements are embedded into the thickness of the bottom wall 204 of housing base 206, so that they would not be visible from below (see FIG. 14) even though the silicone overmolded skirt 208 is transparent. However, the discrete letters 202 would clearly be visible on an X-ray very similarly to the port assembly shown in FIG. 11. Another manner of using discrete letters 202 is depicted in FIGS. 16 to 18, in which the letters 202 are insert molded along the bottom surface 230 of housing base 232 and recessed thereinto, preferably. With this variant, the radiopaque material may be titanium or may be, for example, silicone material having barium sulfate filler. In this case the mirror-image of "CT" would be visible from below as depicted in FIG. 18 after the silicone overmolding of skirt 234 about the exterior of housing base 232.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. An implantable venous access port assembly, comprising:
   a needle-penetrable septum; and
   a housing securing the needle-penetrable septum, at least a portion of the housing comprising a radiopaque material, at least one cutout defined in at least a portion of the radiopaque material, the at least one cutout forming at least one X-ray discernable indicium indicative of an attribute of the access port assembly.

2. The port assembly of claim 1, wherein the radiopaque material comprises a generally planar portion recessed into a bottom surface of a bottom wall of the housing, the generally planar portion including the at least one cutout.

3. The port assembly of claim 1, wherein:
the attribute is a pressure property of the port assembly.

4. The port assembly of claim 3, wherein the pressure property is the port assembly being rated to be used for power injection.

5. The port assembly of claim 3, wherein the pressure property is the port assembly can withstand pressures for injection of contrast fluid.

6. The port assembly of claim 1, wherein the radiopaque material comprises titanium.

7. The port assembly of claim 1, wherein the radiopaque material comprises a polymer with a radiopaque filler.

8. The port assembly of claim 1, wherein the housing further comprises a skirt formed from radiotransparent material molded about at least a portion of the housing.

9. The port assembly of claim 1, wherein the at least one X-ray discernable indicium comprise at least one alphabetical letter.

10. The port assembly of claim 9, wherein the at least one alphabetical letter is at least one of "C" and "T".

11. The port assembly of claim 1, wherein at least a portion of the housing is made of polysulfone resin.

12. The port assembly of claim 1, wherein the housing and the septum define a reservoir, and at least a portion of the radiopaque material is projecting outward of a periphery of the reservoir.

13. The port assembly of claim 1, wherein the housing comprises entirely of the radiopaque material.

14. The port assembly of claim 1, wherein the housing further comprises a material of different radiopacity from the radiopaque material.

15. An implantable venous access port assembly, comprising:
a needle-penetrable septum; and
a housing securing the needle-penetrable septum, the housing comprising X-ray discernable indicia formed through a portion of the port assembly, at least one of the X-ray discernable indicia being visible in mirror-image orientation from a bottom of the port assembly.

16. The port assembly of claim 15, wherein the X-ray discernable indicia indicate an attribute of the port assembly.

17. The port assembly of claim 16, wherein the attribute is a pressure property of the port assembly.

18. The port assembly of claim 17, wherein the pressure property is the port assembly being rated to be used for power injection.

19. The port assembly of claim 17, wherein the pressure property is the port assembly can withstand pressure used for injection of contrast fluid.

20. The port assembly of claim 15, further comprising a radiopaque material, wherein the X-ray discernable indicia are formed as at least one cutout in the radiopaque material.

21. The port assembly of claim 20, wherein the radiopaque material comprises titanium.

22. The port assembly of claim 20, wherein the radiopaque material comprises a polymer with a radiopaque filler.

23. The port assembly of claim 20, wherein the housing further comprises a skirt formed from radiotransparent material molded about at least a portion of the housing.

24. The port assembly of claim 20, wherein the radiopaque material comprises a generally planar portion recessed into a bottom surface of a bottom wall of the housing.

25. The port assembly of claim 20, wherein the housing comprises entirely of the radiopaque material.

26. The port assembly of claim 20, wherein the housing comprises a material of different radiopacity from the radiopaque material.

27. The port assembly of claim 15, wherein the X-ray discernable indicia comprise at least one alphabetical letter.

28. The port assembly of claim 27, wherein the at least one alphabetical letter is at least one of "C" and "T".

29. The port assembly of claim 15, wherein at least a portion of the housing is made of polysulfone resin.

30. The port assembly of claim 15, wherein the housing and the septum define a reservoir, and at least a portion of the X-ray discernable indicia is projecting outward of a periphery of the reservoir.

* * * * *